US012606778B2

(12) United States Patent
Agarkhed et al.

(10) Patent No.: US 12,606,778 B2
(45) Date of Patent: Apr. 21, 2026

(54) SOAP BAR

(71) Applicant: Conopco, Inc., Englewood Cliffs, NJ (US)

(72) Inventors: Ajit Manohar Agarkhed, Thane (IN); Himanshu Akre, Mumbai (IN); Amalendu Bangal, Dist-Paschim Midnapore (IN); Chandra Sekhar Ghosh, Howraw (IN); Siva Rama Krishna Perala, Bangalore (IN); Saswati Pujari, Bangalore (IN); Yuriy Konstantinovich Yarovoy, Monroe, CT (US)

(73) Assignee: Conopco, Inc., Hoboken, NJ (US)

( * ) Notice: Subject to any disclaimer, the term of this patent is extended or adjusted under 35 U.S.C. 154(b) by 235 days.

(21) Appl. No.: 18/278,020

(22) PCT Filed: Feb. 25, 2022

(86) PCT No.: PCT/EP2022/054832
§ 371 (c)(1),
(2) Date: Aug. 21, 2023

(87) PCT Pub. No.: WO2022/180228
PCT Pub. Date: Sep. 1, 2022

(65) Prior Publication Data
US 2024/0060017 A1 Feb. 22, 2024

(30) Foreign Application Priority Data
Feb. 26, 2021 (EP) ..................................... 21159699

(51) Int. Cl.
| | |
|---|---|
| *C11D 9/00* | (2006.01) |
| *A61K 8/04* | (2006.01) |
| *A61K 8/26* | (2006.01) |
| *A61K 8/36* | (2006.01) |
| *A61Q 19/10* | (2006.01) |
| *C11D 9/10* | (2006.01) |
| *C11D 13/10* | (2006.01) |
| *C11D 13/18* | (2006.01) |

(52) U.S. Cl.
CPC ................ *C11D 9/10* (2013.01); *A61K 8/042* (2013.01); *A61K 8/26* (2013.01); *A61K 8/361*
(2013.01); *A61Q 19/10* (2013.01); *C11D 13/10* (2013.01); *C11D 13/18* (2013.01)

(58) Field of Classification Search
None
See application file for complete search history.

(56) References Cited

U.S. PATENT DOCUMENTS

| | | |
|---|---|---|
| 2,677,665 A | 5/1954 | James |
| 2,798,053 A | 7/1957 | Brown |
| 4,213,950 A | 7/1980 | Mahler |
| 4,719,030 A | 1/1988 | Williams et al. |
| 5,362,466 A | 11/1994 | Araya |
| 2004/0034164 A1 | 2/2004 | Melchiors et al. |
| 2004/0254088 A1 | 12/2004 | Ruijter et al. |

FOREIGN PATENT DOCUMENTS

| | | | | |
|---|---|---|---|---|
| AT | 322511 | 4/2006 | | |
| CN | 1107111 | 4/2003 | | |
| CN | 1806039 | 7/2006 | | |
| EP | 0384070 | 8/1990 | | |
| EP | 1184338 | 3/2002 | | |
| EP | 1141216 | 2/2006 | | |
| GB | 1571004 | 7/1980 | | |
| GB | 2316069 | 2/1998 | | |
| KR | 20040035953 | 4/2004 | | |
| WO | WO9513356 | 5/1995 | | |
| WO | WO9513357 | 5/1995 | | |
| WO | WO-0036075 A1 * | 6/2000 | ............ | C11D 11/04 |
| WO | WO2006094586 | 9/2006 | | |
| WO | WO2020169409 | 8/2020 | | |

OTHER PUBLICATIONS

Search Report and Written Opinion in EP21159699; Aug. 27, 2021; European Patent Office (EPO).
Search Report and Written Opinion in PCTEP2022054832; May 23, 2022; World Intellectual Property Org. (WIPO).
IPRP2 in PCTEP2022054832; Feb. 7, 2023; World Intellectual Property Org. (WIPO).

* cited by examiner

*Primary Examiner* — Necholus Ogden, Jr.
(74) *Attorney, Agent, or Firm* — Krista J. Aiello

(57) ABSTRACT

The present invention relates to an extruded soap bar composition. It more particularly relates to a soap bar composition which comprises specified type of sodium alumino silicate gel to produce soap bars with high water content that are not only easy to extrude but have the desired hardness.

15 Claims, No Drawings

SOAP BAR

CROSS REFERENCE TO RELATED APPLICATIONS

The present application is a U.S. National Phase Application under 35 U.S.C. § 371 of International Application No. PCT/EP2022/054832, filed on Feb. 25, 2022, which claims priority to European Patent Application No. 21159699.4, filed on Feb. 26, 2021, the contents of which are incorporated herein in their entireties.

FIELD OF THE INVENTION

The present invention relates to a soap bar composition. It more particularly relates to a soap bar composition that comprises high amount of water and yet exhibits sufficient hardness such that it is easy to extrude and stamp.

BACKGROUND OF THE INVENTION

Surfactants have been used for personal wash applications for a long time. There are many categories of products in the personal wash market e.g. body wash, face wash, hand wash, soap bars and shampoos. Products which are marketed as body wash, face wash and shampoos are generally in liquid form and are made of synthetic anionic surfactants. They are generally sold in plastic bottles/containers. Soap bars and hand wash products generally contain soaps. Soap bars do not need to be sold in plastic containers and are able to retain their own shape by virtue of being structured in the form of a rigid solid. Soaps bars are usually sold in cartons made of cardboard.

Other than application for personal washing, soaps are also used for laundering clothes, and such soaps are commonly referred to as laundry bars. Laundry bars designed for washing fabrics are formulated to provide effective cleaning in clothes, acceptable sudsing characteristics, slow wear rates, good hardness, durability and low smear properties.

Laundry bar compositions may include soap, synthetic detergent or a combination of soap and synthetic detergent as the main detersive surfactant. In some regions soap-based laundry bars are preferred for laundering fabrics. Laundry soap bar compositions typically contain 60 wt. % to 80 wt. % soaps and around 14 wt. % to 22 wt. % of water and optionally small amounts of inorganic salt and filler.

Soap bars whether for personal wash purposes or for laundering clothes, are generally prepared through one of two routes. One is called the cast bar route while the other is called the milled and plodded route (also known as extrusion route). The cast bar route has inherently been very amenable in preparing low TFM (total fatty matter) bars. Total fatty matter is a common way of defining the quality of soap. TFM is defined as the total amount of fatty matter, mostly fatty acids, that can be separated from a sample of soap after splitting with a mineral acid, usually hydrochloric acid. In the cast bar soaps, the soap mixture is mixed with polyhydric alcohols and poured in casts and allowed to cool and then the soap bars are removed from the casts. The cast bar route enables production at relatively lower throughput rates.

In the milled and plodded route, the soap is prepared with high water content and then spray dried to reduce the moisture content and to cool the soap after which other ingredients are added and then the soap is extruded through a plodder and optionally cut and stamped to prepare the final soap bar. The milled and plodded soaps generally have a high TFM in the range of 60 to 80 weight percent.

Milled and plodded soap bars are also known as extruded soap bars. They are composed of very many different types of soaps. Most soap compositions comprise both water insoluble as well as water soluble soaps. Their structure is generally characterized by a brick and mortar type structure. Insoluble soaps (called bricks) usually consist of higher chain C16 and C18 soaps (palmitate and stearate soap). They are generally included in soap bars to provide structuring benefits i.e they provide shape to the bars. Soap bars also consist of water soluble soaps (which act as the mortar) which are generally unsaturated C18:1 and 18:2 sodium soap (oleate soap) in combination with short chain fatty acids (generally C8 to C12 or even up to C14 soap). Water soluble soaps generally aid in cleaning.

In addition to about the 60-80 wt % TFM, soap bars presently prepared through the extruded route for personal wash contain about 14-22 wt % water. There is a need for developing sustainable technologies where one approach is to develop soaps with lower TFM content and by increasing the water content with no compromise on the cleaning efficacy. The present inventors are aware of various attempts by the present applicants and others to reduce the fatty matter content. These technologies include approaches to structure soap bars, like inclusion of aluminium phosphate or insitu generation of calcium silicate. Such technologies are not very skin friendly and so are not appropriate for personal washing or for washing fabric by hand. If one simply substitutes the TFM with higher amount of water, it causes problems during extrusion of the soap mass and further the extruded bars are sticky and cannot be stamped easily. The present inventors are also aware of various other approaches including inclusion of natural aluminosilicate clays like bentonite or kaolinite but they are found to not be very efficient in structuring the bars at low amounts.

The present applicant has also included zeolite in soap bars to increase the water content e.g. as published in WO2020/169409. Although this technology enables the production of soap bars containing 22 to 35 wt % water, the search is on to develop soap bars that can contain higher amounts of water and yet deliver all the desired consumer benefits. The present inventors with their extensive research experience in the area of alumino silicate gels, were able to develop even better water holding soap bars by incorporating in them, specific alumino silicate gel where the $SiO_2/Al_2O_3$ mole ratio is less than 5.0.

Alumino silicate gels have been incorporated in soap bars but the gels so incorporated were not in the presently claimed $SiO_2/Al_2O_3$ mole ratio and therefore those soaps bars do not exhibit the high water holding capacity and so are not extrudable in a conventional plodder.

U.S. Pat. No. 2,677,665 (Unilever, 1954) discloses a method of forming hard solid filled soap product which includes the steps of chilling hot molten filled soap containing sodium aluminum silicate gel and thereafter plodding the resultant solidified filled soap. The present inventors have calculated that the soap disclosed in this patent uses sodium aluminium silicate where the $SiO_2/Al_2O_3$ mole ratio is higher than that claimed in the present invention and therefore does not deliver the requisite water holding capacity.

It is thus an object of the present invention to provide for a soap bar composition comprising high amount of water in the range of 15 to 45 wt % which can be prepared using the extrusion route and is easily and conveniently stampable.

SUMMARY OF THE INVENTION

In a first aspect, the present invention relates to a soap bar comprising
(i) 18 to 75 wt % soap;
(ii) 1.0 to 15.0 wt % sodium alumino silicate gel;
(iii) 15 to 45, preferably 22 to 40 wt % water;
wherein the $SiO_2/Al_2O_3$ mole ratio of the sodium alumino silicate gel is less than 5.0.

In a second aspect, the present invention relates to a process to prepare a soap bar of the first aspect comprising the steps of:
(a) providing soap,
(b) providing sodium aluminate
(c) providing sodium silicate
(d) mixing the soap and a mixture of sodium aluminate and sodium silicate; and
(e) extruding the mixture to prepare the desired soap bar.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The present invention relates to a soap bar composition. By a soap bar composition is meant a cleansing composition comprising soap which is in the form of a shaped solid. The soap bar of the invention is especially useful for personal cleansing. When the soap bar of the present invention is for personal washing application it comprises 18 to 75% total amount of soap, preferably 25 to 75%, more preferably 35 to 70 and most preferably 50 to 70% by weight of the soap bar. When the soap bar of the invention is for laundering fabrics, it comprises from 15 wt. % to 60 wt. % fatty acid soap. Preferred aspects of such soap bars comprise at least 20 wt. %, preferably at least 25 wt. %, still preferably at least 30 wt. % and most preferably at least 35 wt. %, but typically not more than 58 wt. %, still preferably not more than 55 wt. %, still further preferably not more than 53 wt. %, still more preferably not more than 50 wt. %, and most preferably not more than 45 wt. % fatty acid soap in the soap bar composition.

The term soap means salt of fatty acid. Preferably, the soap is soap of C8 to C24 fatty acids.

The cation may be an alkali metal, alkaline earth metal or ammonium ion, preferably alkali metals. Preferably, the cation is selected from sodium or potassium, more preferably sodium. The soap may be saturated or unsaturated. Saturated soaps are preferred over unsaturated soaps for stability. The oil or fatty acids may be of vegetable or animal origin.

The soap may be obtained by saponification of oils, fats or fatty acids. The fats or oils generally used to make soap bars may be selected from tallow, tallow stearins, palm oil, palm stearins, soya bean oil, fish oil, castor oil, rice bran oil, sunflower oil, coconut oil, babassu oil, and palm kernel oil. The fatty acids may be from coconut, rice bran, groundnut, tallow, palm, palm kernel, cotton seed or soyabean.

The fatty acid soaps may also be synthetically prepared (e.g. by the oxidation of petroleum or by the hydrogenation of carbon monoxide by the Fischer-Tropsch process). Resin acids, such as those present in tall oil, may also be used. Naphthenic acids may also be used.

The soap bar may additionally comprise synthetic surfactants selected from one or more from the class of anionic, non-ionic, cationic or zwitterionic surfactants, preferably from anionic surfactants. These synthetic surfactants, as per the present invention, are included in less then 8%, preferably less then 4%, more preferably less then 1% and sometimes absent from the composition. By By "absent" it is meant that there is no deliberately added synthetic surfactant in the soap bar composition of the present invention.

The composition of the present invention is in the form of a shaped solid for example a bar. The cleaning soap composition is a wash off product that generally has sufficient amount of surfactants included therein that it is used for cleansing the desired topical surface e.g. the whole body, the hair and scalp or the face. It is applied on the topical surface and left thereon only for a few seconds or minutes and washed off thereafter with copious amounts of water.

The soap bars of the present invention preferably include low molecular weight soaps (C8 to C14 soaps) which are generally water soluble, which are in the range of 2 to 20% by weight of the composition. It is preferred that the soap bar includes 15 to 55 wt % of the soap of C16 to C24 fatty acid, which are generally water insoluble soaps. Unsaturated fatty acid soaps preferably at 15 to 42% may also be included in the total soap content of the composition. Unsaturated soaps are preferably oleic acid soaps.

The composition of the invention comprises selective amount of a sodium alumino silicate gel having a specific molar ratio of $SiO_2/Al_2O_3$. Sodium alumino silicate gel is preferably included in 2 to 10%, more preferably 2 to 7% by weight of the composition. The sodium alumino silicate gel is carefully prepared such that the molar ratio of $SiO_2/Al_2O_3$ is less than 5.0, preferably less than 3.5.

The soap bar of the invention is capable of stably retaining high amount of water in the range of 15 to 45 wt % as compared to conventional soap bar. Thus, water is preferably at least 18 wt. %, further preferably at least 20 wt. %, still more preferably at least 23 wt. % furthermore preferably at least 25 wt. % but the amount of water in the soap bar composition is preferably not more than 40 wt. %, still preferably not more than 38 wt. %, most preferably not more than 35 wt. %. In highly preferred aspects, the amount of water in the soap composition ranges from 21 to 40%, more preferably 23 to 40% by weight of the composition. Without wishing to be bound by theory, the inventors believe that aluminosilicate gel structuring provides a more rigid mortar and harder bricks as compared to without aluminosilicate gel structuring at comparable moisture level in the soap bar. The rigid mortar is believed to be due to caging of water in the aluminosilicate by hydrogen bonding while harder bricks is believed to be obtained due to efficient interaction between soap and amorphous submicron size particles present in the gel.

Optional Ingredients in Soap Bars

The soaps bar composition may optionally comprise 0.1 to 15%, preferably 0.2 to 12% by weight of free fatty acids. By free fatty acids is meant a carboxylic acid comprising a hydrocarbon chain and a terminal carboxyl group bonded to an H. Suitable fatty acids are C8 to C22 fatty acids. Preferred fatty acids are C12 to C18, preferably predominantly saturated, straight-chain fatty acids. However, some unsaturated fatty acids can also be employed.

The composition preferably comprises a polyhydric alcohol (also called polyol) or mixture of polyols. Polyol is a term used herein to designate a compound having multiple hydroxyl groups (at least two, preferably at least three) which is highly water soluble. Many types of polyols are available including: relatively low molecular weight short chain polyhydroxy compounds such as glycerol and propylene glycol; sugars such as sorbitol, manitol, sucrose and glucose; modified carbohydrates such as hydrolyzed starch, dextrin and maltodextrin, and polymeric synthetic polyols such as polyalkylene glycols, for example polyoxyethylene glycol (PEG) and polyoxypropylene glycol (PPG). Especially preferred polyols are glycerol, sorbitol and their mixtures. Most preferred polyol is glycerol. In a preferred embodiment, the bars of the invention comprise 0 to 8%, preferably 1 to 7.5% by wt. polyol.

The soap bar composition generally comprises electrolyte and water. Electrolytes as per this invention include compounds that substantially dissociate into ions in water. Electrolytes as per this invention are not an ionic surfactant. Suitable electrolytes for inclusion in the soap making process are alkali metal salts. Preferred alkali metal salts include sodium sulfate, sodium chloride, sodium acetate, sodium citrate, potassium chloride, potassium sulfate, sodium carbonate and other mono or di or tri salts of alkaline earth metals, more preferred electrolytes are sodium chloride, sodium sulfate, sodium citrate, potassium chloride and especially preferred electrolyte is sodium chloride sodium sulphate, sodium citrate or a combination thereof. For the avoidance of doubt, it is clarified that the electrolyte is a non-soap material. Electrolyte is preferably included in 0.1 to 6%, more preferably 0.5 to 6%, even more preferably 0.5 to 5%, furthermore preferably 0.5 to 3%, and most preferably 1 to 3% by weight of the composition. It is preferred that the electrolyte is included in the soap bar during the step of saponification to form the soap.

The various optional ingredients that make up the final soap bar composition are as described below:

The total level of the adjuvant materials used in the bar composition generally is in an amount not higher than 50%, preferably 1 to 50%, more preferably 3 to 45% by wt. of the soap bar composition.

Suitable starchy materials which may be used include natural starch (from corn, wheat, rice, potato, tapioca and the like), pregelatinzed starch, various physically and chemically modified starch and mixtures thereof. By the term natural starch is meant starch which has not been subjected to chemical or physical modification—also known as raw or native starch. The raw starch can be used directly or modified during the process of making the bar composition such that the starch becomes gelatinized, either partially or fully gelatinized. Such starchy materials are commercially available e.g. FARMAL® CS 3400 (corn starch) and FARMAL® WS 4400 (corn starch; waxy unmodified).

The adjuvant system may optionally include insoluble particles comprising one or a combination of materials. By insoluble particles is meant materials that are present in solid particulate form and suitable for personal washing. Preferably, there are mineral (e.g., inorganic) or organic particles.

The insoluble particles should not be perceived as scratchy or granular and thus should have a particle size less than 300 microns, more preferably less than 100 microns and most preferably less than 50 microns.

Preferred inorganic particulate material includes talc and calcium carbonate. Talc is a magnesium silicate mineral material, with a sheet silicate structure and a composition of $Mg_3Si_4(OH)_{22}$ and may be available in the hydrated form. It has a plate-like morphology, and is essentially oleophilic/hydrophobic, i.e., it is wetted by oil rather than water.

Calcium carbonate or chalk exists in three crystal forms: calcite, aragonite and vaterite. The natural morphology of calcite is rhombohedral or cuboidal, acicular or dendritic for aragonite and spheroidal for vaterite.

Examples of other optional insoluble inorganic particulate materials include aluminates, silicates, phosphates, insoluble sulfates, borates and clays (e.g., kaolin, china clay) and their combinations.

Organic particulate materials include: insoluble polysaccharides such as highly crosslinked or insolubilized starch (e.g., by reaction with a hydrophobe such as octyl succinate) and cellulose; synthetic polymers such as various polymer lattices and suspension polymers; insoluble soaps and mixtures thereof.

It is preferred that the compositions of the invention comprise polymers. Polymers of the acrylate class are especially preferred. Preferred bars include 0.05 to 5% acrylates. More preferred bars include 0.01 to 3% acrylates. Examples of acrylate polymers include polymers and copolymers of acrylic acid crosslinked with polyallylsucrose as described in U.S. Pat. No. 2,798,053 which is herein incorporated by reference. Other examples include polyacrylates, acrylate copolymers or alkali swellable emulsion acrylate copolymers, hydrophobically modified alkali swellable copolymers, and crosslinked homopolymers of acrylic acid. Examples of such commercially available polymers are: ACULYN®, CARBOPOL®, and CARBOPOL® Ultrez grade series.

Bar compositions preferably comprise 0.1 to 25% by wt. of bar composition, preferably 5 to 15 by wt. of these mineral or organic particles.

An opacifier may be optionally present in the personal care composition. When opacifiers are present, the cleansing bar is generally opaque. Examples of opacifiers include titanium dioxide, zinc oxide and the like. A particularly preferred opacifier that can be employed when an opaque soap composition is desired is ethylene glycol mono- or di-stearate, for example in the form of a 20% solution in sodium lauryl ether sulphate. An alternative opacifying agent is zinc stearate.

The product can take the form of a water-clear, i.e. transparent soap, in which case it will not contain an opacifier.

The pH of preferred soaps bars of the invention is from 8 to 11, more preferably 9 to 11.

A preferred bar may additionally include up to 30 wt % benefit agents. Preferred benefit agents include moisturizers, emollients, sunscreens and anti-ageing compounds. The agents may be added at an appropriate step during the process of making the bars. Some benefit agents may be introduced as macro domains.

Other optional ingredients like anti-oxidants, perfumes, polymers, chelating agents, colourants, deodorants, dyes, enzymes, foam boosters, germicides, anti-microbials, lathering agents, pearlescers, skin conditioners, stabilizers or superfatting agents, may be added in suitable amounts in the process of the invention. Preferably, the ingredients are added after the saponification step. Sodium metabisulphite, ethylene diamine tetra acetic acid (EDTA), borax or ethylene hydroxy diphosphonic acid (EHDP) are preferably added to the formulation.

The composition of the invention could be used to deliver antimicrobial benefits. Antimicrobial agents that are preferably included to deliver this benefit include oligodynamic metals or compounds thereof. Preferred metals are silver, copper, zinc, gold or aluminium. Silver is particularly preferred. In the ionic form it may exist as a salt or any compound in any applicable oxidation state. Preferred silver compounds are silver oxide, silver nitrate, silver acetate, silver sulfate, silver benzoate, silver salicylate, silver carbonate, silver citrate or silver phosphate, with silver oxide, silver sulfate and silver citrate being of particular interest in one or more embodiments. In at least one preferred embodiment the silver compound is silver oxide. Oligodynamic metal or a compound thereof is preferably included in 0.0001 to 2%, preferably 0.001 to 1% by weight of the composition. Alternately an essential oil antimicrobial active may be included in the composition of the invention. Preferred essential oil actives which may be included are terpineol, thymol, carvacol, (E)-2(prop-1-enyl) phenol, 2-propylphenol, 4-pentylphenol, 4-sec-butylphenol, 2-benzyl phenol, eugenol or combinations thereof. Furthermore preferred essential oil actives are terpineol, thymol, carvacrol or thymol, most preferred being terpineol or thymol and ideally a combination of the two. Essential oil actives are preferably included in 0.001 to 1%, preferably 0.01 to 0.5% by weight of the composition.

In soap bars for laundering fabric, one or more of the above described optional ingredients may be included. However, in laundry bars, antimicrobial agents are generally not added. Laundry bars generally include chelating agents that are generally not included in soap bars for personal cleansing. Chelating agents may be selected from but not limited to ethylene diamine tetra acetic acid (EDTA), ethylene hydroxy diphosphonic acid (EHDP) or mixtures thereof. The chelating agent is preferably present in an amount ranging from 0.01 wt. % to 1 wt. %. Non-phosphate chelating agents like methylglycinediacetic acid and salts thereof are also preferred.

Process

In a second aspect, the present invention relates to a process to prepare a soap bar of the first aspect comprising the steps of:
  (a) providing soap,
  (b) providing sodium aluminate
  (c) providing sodium silicate
  (d) mixing the soap and a mixture of sodium aluminate and sodium silicate; and
  (e) extruding the mixture to prepare the desired soap bar.
The soap composition may be made into a bar by a process that first involves saponification of the fat charge with alkali followed by extruding the mixture in a conventional plodder. The plodded mass may then be optionally cut to a desired size and stamped with a desirable indicia. An especially important benefit of the present invention is that, notwithstanding the high amount of water content of the soap bar, compositions thus prepared by extrusion are found to be easy to stamp with a desirable indicia. By "easy to extrude" is meant that the hardness of the bar as it is extruded is high enough that it exits the extruder in a firm enough form that it can be called a rigid bar. The hardness of the bar is preferably higher than 1.2 kg, more preferably in the range of 1.2 to 5.0 kg (at 40° C.). The hardness is preferably measured using the TA-XT Express apparatus available from Stable Micro Systems. The hardness is measured using this apparatus with a 30° conical probe—Part #P/30c to a penetration of 15 mm. If the soap mass is too soft and is passed through the extruder it will not extrude out of the extruder in a cohesive enough mass to be called a bar. By "easy to stamp" is meant that the soap bar is of such a consistency and low enough stickiness that it does not stick to the die that is used to stamp any desired indicia on the bar. The soap bar prepared by the process of the invention therefore preferably comprises an indicium stamped thereupon.

The specific process that may be employed using the above described general process for soap bar manufacture comprises one of the following processes.

Preferably, the process to prepare the soap bar of the present invention comprises the steps of (a) including sodium alumino silicate gel in a sigma mixer; (b) including soap into the sigma mixer to crush and blend the sodium alumino silicate gel with the soap to prepare a noddle; and (c) extruding the noddle through a plodder to prepare the desired soap bar. In this aspect, one preferred step comprises preparing the sodium alumino silicate gel outside the sigma mixer by reacting the desired amount of sodium aluminate with sodium silicate. In an alternative aspect the sodium alumino silicate is prepared insitu in the sigma mixer by reacting the desired amount of sodium aluminate with sodium silicate.

In another preferred aspect, the process to prepare the soap bar of the present invention comprises the steps of (a) preparing soap in a plough share mixer or crutcher by reacting desired amount of fatty acid/ oil with alkali at 90 to 110° C.; (b) including sodium alumino silicate gel in the plough share mixer or crutcher to mix with the soap so formed in step (a) with said gel to prepare a mixture; (c) spray drying the mixture or passing it through a triple roll mill; and (d) then passing it though a plodder to prepare the desired soap bar.

In yet another aspect, preferably, the process to prepare the soap bar of the present invention comprises the steps of (a) preparing the sodium alumino silicate is insitu in a plough share mixer or crutcher by reacting the desired amount of sodium aluminate with sodium silicate; followed by (b) preparing soap in the same plough share mixer or crutcher by reacting desired amount of fatty acid/oil with alkali at 90 to 110° C. with constant agitation to prepare a mixture; (c) spray drying the mixture or passing it through a triple roll mill; and (d) then passing it though a plodder to prepare the desired soap bar.

The sodium alumino silicate gel and the various methods by which it can be prepared and incorporated in the soap is described below.

Sodium alumino silicate gel is sometimes referred to in common parlance as zeolite gel. It is prepared by reacting sodium silicate and sodium aluminate in aqueous medium. The gel can be prepared separately in a mixer for incorporation in the soap. Such a process is known as premade gel route. Alternately the gel can be prepared in the same process step (and reactor) where the saponification of soap take place and such a process is known as the in-situ route. The gel could be incorporated or made in situ in any of the soap processing equipment known in the art e.g., sigma mixer, plough shear mixer, or the crutcher. Preferred processes by which the gel is incorporated in soap in the present invention are detailed below:

Method 1 (Pre-Made Gel Route)

In this method the gel is prepared separately and added to the soap either during the stage of saponification of oil (or fatty acids) or during the finishing line.

Gel Preparation

The required amount of sodium silicate and water is taken in a container under mixing at about 250-300 rpm. Calculated amount of aqueous sodium aluminate is slowly added under mixing condition. The mixing may be continued for about 15 minutes.

Extrusion of Soap with the Premade Zeolite Gel

The premade gel can to be added to the soap after complete saponification of oil (or neutralization of fatty acids) in the plough shear mixer (PSM)/Crutcher or in the finishing line (e.g. I the sigma mixer). The mass is then milled through a triple roll mill. The mass is then added to the plodder to extrude the soap in the shape of a billet.

Method 2 (In-Situ Gel Route)

In this route gel is prepared in the soap making equipment e.g., in the PSM, the crutcher, or the sigma mixer.

In-Situ Gel Route in PSM/Crutcher

The required amount of fatty acids/oil blend is taken in a PSM/Crutcher and then it is heated to about 90 to 110° C. and it is neutralized by adding stoichiometric amount of alkali. Prediluted aqueous solution of sodium silicate is added and allowed to mix for some time. Thereafter, aqueous solution of sodium aluminate is added slowly under mixing conditions. The soap mass is then taken out of the mixer and passed through either a triple roll mill if the mass come from a PSM or spray dried if the mass comes from a crutcher. The mass is then passed into a plodder to extrude the soap in the shape of a billet.

In-Situ Gel Route in Sigma Mixer

Soap noodles are taken in a sigma mixer to crush the noodles. Under mixing conditions, pre-diluted sodium silicate is slowly added into the crushed noodles. Sodium Aluminate is then slowly added under mixing conditions. The soap mass is then taken out of the mixer and this is milled by passing the mass through a triple roll mill. The mass is then added into a plodder and the soap is then extruded in the shape of a billet.

An alternate route to prepare this is as follows. Required amount of sodium silicate and water are taken in a PSM/Crutcher and required amount of sodium aluminate is added slowly under mixing conditions for some time. Thereafter required amount of fatty acids/oil blend is taken into it and neutralized by adding stoichiometric amount of alkali for desired amount of time of mixing. The mass is then taken out and spray dried or passed through a triple roll mill before passing through a plodder to get the mass in the shape of a bar.

Preparation of the Sodium Alumino Silicate Gel

The Sodium Alumino Silicate Gel can be prepared separately (calling it as ex-situ or premade) and can also be prepared in the presence of soap (calling it as in-situ).

Specific example of preparation of ex-situ Sodium Alumino Silicate Gel

To prepare a Sodium Alumino Silicate Gel of $SiO_2/Al_2O_3$ mole ratio 2.05 following sequence of addition and conditions are followed:

a. Required quantity (1083 gm as 45% aqueous solution) of sodium silicate solution is taken in a 5 lit plastic beaker b. Required quantity (2103 gm) of process water is added slowly under stirring condition (350 rpm) using an overhead stirrer c. Required quantity (1083 gm as 45% aqueous solution) of sodium aluminate solution is added slowly into the prediluted aqueous solution of sodium silicate keeping stirrer on d. The aqueous mixture in the form of gel is allowed to mix for another 5 min at high speed (500 rpm).

In-situ Sodium Alumino Silicate Gel

For preparing Sodium Alumino Silicate Gel of $SiO_2/Al_2O_3$ mole ratio 2.05 following sequence of addition and conditions are followed:

a. Required quantity (24157 gm) of 17% water containing soap noodle is crushed in the sigma mixer for 5 min b. Required quantity (1083 gm as 45% aqueous solution) of sodium silicate solution is taken in a 5 lit of plastic beaker c. Required quantity of process water (2103 gm) is added slowly under stirring condition (350 rpm) using an overhead stirrer d. The prediluted aqueous solution of sodium silicate is added slowly into the pre-crushed soap noodle keeping sigma mixer on and whole mass is allowed to mix for 2 min e. Required quantity (1083 gm as 45% aqueous solution) of sodium aluminate solution is added into the mass keeping sigma mixer on and allowed to mix for another 4 min The invention will now be illustrated by means of the following non-limiting examples.

EXAMPLES

Example A-F and 1-2

Effect of Soap Bars Outside and Within the Invention on Extrudability

The following eight soap bar compositions as shown in Table—1 were prepared. Examples A-F were soap compositions which were prepared as per Examples 1-6 given in U.S. Pat. No. 267,765. Examples 1-2 were soap compositions prepared as per the present invention.

TABLE 1A

| Ingredient (wt %) | A | B | C | D | E | F | 1 | 2 |
|---|---|---|---|---|---|---|---|---|
| Soap (68%) | 63.0 | 63.0 | 55.0 | 84.0 | 69.0 | 63.0 | 82.5 | 82.5 |
| Soap (dry basis) | 42.9 | 42.9 | 37.4 | 57.2 | 46.9 | 42.8 | 56.1 | 56.1 |
| Glycerine | 4.29 | 4.29 | 3.74 | 5.72 | 4.69 | 4.28 | — | — |
| Neutral sodium silicate (40%) | 27.0 | 27.0 | 35.0 | 11.7 | 22.5 | 27.0 | — | — |
| Neutral sodium silicate (dry basis) | 10.8 | 10.8 | 14.0 | 4.68 | 9.0 | 10.8 | — | — |
| Alkaline sodium silicate (30%) | — | — | — | — | — | — | 9.0 | 12.6 |
| Alkaline sodium silicate (dry basis) | — | — | — | — | — | — | 2.7 | 3.78 |
| Sodium aluminate (40%) | 10.0 | 10.0 | 10.0 | 4.3 | 8.5 | 10.0 | 9.00 | 5.4 |
| Sodium aluminate (dry weight basis) | 4.0 | 4.0 | 4.0 | 1.72 | 3.4 | 4.0 | 3.6 | 2.16 |
| Others | 2.50 | 4.00 | — | — | — | 4.00 | — | — |
| Electrolyte | — | — | — | — | — | — | 2.5 | 2.5 |
| Water | 35.51 | 34.01 | 40.86 | 30.68 | 36.01 | 34.12 | 35.1 | 35.54 |
| Gel (wt %) | 14.8 | 14.8 | 18.0 | 6.4 | 12.4 | 14.8 | 6.3 | 5.9 |

TABLE 1A-continued

| Ingredient (wt %) | A | B | C | D | E | F | 1 | 2 |
|---|---|---|---|---|---|---|---|---|
| $SiO_2/Al_2O_3$ mole ratio | 6.6 | 6.6 | 8.6 | 6.6 | 6.1 | 6.6 | 1.6 | 3.7 |
| Extrudability | Poor | Poor | Poor | Poor | Poor | Poor | Good | Good |

TABLE 1B

The soap used in the table 1-A above had the following constitution

| Ingredient (wt %) | A | B | C | D | E | F | 1 | 2 |
|---|---|---|---|---|---|---|---|---|
| Sodium palm kernalate | 56.7 | 50.4 | 49.5 | 67.2 | 65.6 | 56.7 | 66.0 | 66.0 |
| Sodium palmitate | 6.3 | — | 5.5 | — | — | 6.3 | 16.5 | 16.5 |
| Sodium oleate | — | 12.6 | — | 16.8 | 3.4 | — | — | — |
| Total soap (68%) | 63.0 | 63.0 | 55.0 | 84.0 | 69.0 | 63.0 | 82.5 | 82.5 |

The data in the above Table 1A indicates that soap bars where the sodium aluminosilicate is included as per the invention (Example 1 and 2) where the $SiO_2/Al_2O_3$ mole ratio is less then 5 are easy to extrude into billets while those bars prepared as disclosed in the prior art (U.S. Pat. No. 267,765) are soft and difficult to extrude.

Examples 3-8

Hardness of Bars Prepared as Per the Invention

Soap bars were prepared as per compositions in Table—2A, below. The sodium aluminosilicate gel was included in the soap during the stage of mixing in the sigma mixer (for examples 3-7) and in the saponification stage (for Example 8).

TABLE 2A

| Ingredient, wt % | Ex - 3 | Ex-4 | Ex-5 | Ex-6 | Ex-7 | Ex-8 |
|---|---|---|---|---|---|---|
| Anhydrous soap* | 68.8 | 66.8 | 65.8 | 65.1 | 53.5 | 66.8 |
| Total water | 23.0 | 25.0 | 25.0 | 25.0 | 37.0 | 25.0 |
| Glycerine | 3.5 | 3.5 | 3.5 | 3.5 | 2.0 | 3.5 |
| Sodium citrate | — | — | 2.0 | 2.0 | — | — |
| Lauric acid | 0.25 | 0.25 | 0.25 | 0.25 | 0.25 | 0.25 |
| Sodium Alumino-Silicate** $[(Na_2O)_x(Al_2O_3)_y(SiO_2)_z]$ | 3.25 | 3.25 | 2.27 | 2.92 | 6.00 | 3.25 |
| Others | To 100 | To 100 | To 100 | To 100 | To 100 | To 100 |
| Sodium aluminate to sodium silicate wt ratio | 50:50 | 50:50 | 50:50 | 40:60 | 50:50 | 50:50 |
| $SiO_2/Al_2O_3$ mole ratio | 2.05 | 2.05 | 2.05 | 3.09 | 2.05 | 2.05 |
| Extrudability of the billet | Good | Good | Good | Good | Good | Good |
| Hardness (kg) of the soap at 40° C. | 3.5 | 3.3 | 2.8 | 3.2 | 2.2 | 3.5 |

*The composition of the anhydrous soap in the above table is as given below in Table 2B

TABLE 2B

| Composition | Wt. % |
|---|---|
| C8 to C14 | 20 |
| C18:1 to C18:3 | 40 |
| C16 to C18 | 38 |
| Sodium Chloride | 0.7 |
| Chelating Agent (Etidronate) | 0.3 |
| EDTA | 0.3 |
| Minors | To 100 |

The hardness of the samples was measured using the procedure described below and the measured values are given above in Table-2A:

Hardness Testing Protocol

Principle

A 30° conical probe penetrates into a soap/syndet sample at a specified speed to a pre-determined depth. The resistance generated at the specific depth is recorded. There is no size or weight requirement of the tested sample except that the bar/billet be bigger than the penetration of the cone (15 mm) and have enough area. The recorded resistance number is also related to the yield stress and the stress can be calculated as noted below. The hardness (and/or calculated yield stress) can be measured by a variety of different penetrometer methods. In this invention, as noted above, we use probe which penetrates to depth of 15 mm.

Apparatus and Equipment

TA-XT Express (Stable Micro Systems)
30° conical probe—Part #P/30c (Stable Micro Systems)

Sampling Technique

This test can be applied to billets from a plodder, finished bars, or small pieces of soap/syndet (noodles, pellets, or bits). In the case of billets, pieces of a suitable size (9 cm) for the TA-XT can be cut out from a larger sample. In the case of pellets or bits which are too small to be mounted in the TA-XT, the compression fixture is used to form several noodles into a single pastille large enough to be tested.

Procedure

Setting up the TA-XT Express
These settings need to be inserted in the system only once. They are saved and loaded whenever the instrument is turned on again. This ensures settings are constant and that all experimental results are readily reproducible.

Set test method

Press MENU
Select TEST SETTINGS (Press 1)
Select TEST TPE (Press 1)
Choose option 1 (CYCLE TEST) and press OK
Press MENU
Select TEST SETTINGS (Press 1)
Select PARAMETERS (Press 2)
Select PRE TEST SPEED (Press 1)
Type 2 (mm s$^{-1}$) and press OK
Select TRIGGER FORCE (Press 2)
Type 5 (g) and Press OK
Select TEST SPEED (Press 3)

Type 1 (mm s$^{-1}$) and press OK
Select RETURN SPEED (Press 4)
Type 10 (mm s$^{-1}$) and press OK
Select DISTANCE (Press 5)
Type 15 (mm) for soap billets or 3 (mm) for soap pastilles and press OK
Select TIME (Press 6)
Type 1 (CYCLE)

Calibration

Screw the probe onto the probe carrier.
Press MENU
Select OPTIONS (Press 3)
Select CALIBRATE FORCE (Press 1)—the instrument asks for the user to check whether the calibration platform is clear
Press OK to continue and wait until the instrument is ready.
Place the 2 kg calibration weight onto the calibration platform and press OK
Wait until the message "calibration completed" is displayed and remove the weight from the platform.

Sample Measurements

Place the billet onto the test platform.
Place the probe close to the surface of the billet (without touching it) by pressing the UP or DOWN arrows.

Press RUN

Take the readings (g or kg) at the target distance (Fin).
After the run is performed, the probe returns to its original position.
Remove the sample from the platform and record its temperature.

Calculation & Expression of Results

Output

The output from this test is the readout of the TA-XT as "force" (RT) in g or kg at the target penetration distance, combined with the sample temperature measurement. (In the subject invention, the force is measured in Kg at 40° C. at 15 mm distance)

The force reading can be converted to extensional stress, according to the equation below:

The equation to convert the TA-XT readout to extensional stress is $$\sigma = \frac{1}{C} \frac{R_T g_c}{A}$$

where: $\sigma$ = extensional stress $C$ = "constraint factor" (1.5 for 30° cone)

$G_c$ = acceleration of gravity $A$ = projected area of cone = $\pi \left( d \tan \frac{1}{2} \theta \right)^2$ $d$ = penetration depth $\theta$ = cone angle For a 30° cone at 15 mm penetration Equation 2 becomes $$\sigma(Pa)=R_T(g)\times 128.8$$

This stress is equivalent to the static yield stress as measured by penetrometer.
The extension rate is $$\dot{\varepsilon} = \frac{V}{d \tan\left(\frac{1}{2}\theta\right)}$$

where $\dot{\varepsilon}$ = extension rate $\left(s^{-1}\right)$ $V$ = cone velocity For a 30° cone moving at 1 mm/s, $\dot{\varepsilon}$ = 0.249 $s^{-1}$

Temperature Correction

The hardness (yield stress) of skin cleansing bar formulations is temperature-sensitive. For meaningful comparisons, the reading at the target distance ($R_T$) should be corrected to a standard reference temperature (normally 40° C.), according to the following equation:

$$R_{40}=R_T\exp\left[\alpha(T-40)\right]$$

where $R_{40}$=reading at the reference temperature (40° C.)
$R_T$=reading at the temperature T
$\alpha$=coefficient for temperature correction
T=temperature at which the sample was analyzed.
The correction can be applied to the extensional stress.

Raw and Processed Data

The final result is the temperature-corrected force or stress, but it is advisable to record the instrument reading and the sample temperature also.
A hardness value of at least 1.2 Kg (measured at 40° C.) is acceptable.
The date in Table—2A above indicates that soap bars with high moisture content can be prepared as per the present invention which extrude well and have high hardness.
Further, compositions as shown in example 9 (sodium alumino silicate in gel form) and example G (sodium alumino silicate in crystalline form (zeolite 4A)) in table 3A below were prepared and their hardness was pleasured using the method described above.

TABLE 3A

| Ingredient, wt % | Ex-9 | Ex-G |
|---|---|---|
| Anhydrous soap* | 53.5 | 53.5 |
| Total water | 34 | 34 |
| Glycerine | 3.6 | 3.6 |
| Sodium citrate | — | — |
| Lauric acid | 0.3 | 0.3 |
| Sodium alumino-silicate gel [$(Na_2O)_x(Al_2O_3)_y(SiO_2)_z$] | 6.5 | — |
| Sodium alumino-silicate (crystalline; Zeolite 4A) | — | 6.5 |
| Others | To 100 | To 100 |
| $SiO_2/Al_2O_3$ mole ratio | 2.1 | 2.1 |
| Extrudability of the billet | Good | Poor |
| Hardness (kg) of the soap at 40° C. | 2.4 | 1.0 (soft mass) |

The data in table 3A above shows that when a soap bar that contained sodium alumino silicate in gel form (example 9) showed better extrudability and hardness as compared to that of a soap bar (example G) which contained the same amounts of sodium aluminosilicate but in crystalline form.
*The composition of the anhydrous soap in table 3A is as given below in Table 3B.

TABLE 3B

| Composition | Wt. % |
|---|---|
| C8 to C14 | 20 |
| C18:1 to C18:3 | 40 |
| C16 to C18 | 38 |
| Sodium Chloride | 0.7 |
| Chelating Agent (Etidronate) | 0.3 |
| EDTA | 0.3 |
| Minors | To 100 |

The invention claimed is:

1. A soap bar comprising
   (i) 18 to 75 wt % soap;
   (ii) 1.0 to 15.0 wt % sodium alumino silicate gel;
   (iii) 15 to 45 22 to 40 wt % water;
   wherein the $SiO_2/Al_2O_3$ mole ratio of the sodium alumino silicate gel is less than 5.0.

2. The soap bar as claimed in claim 1, comprising 35 to 70% wt % soap.

3. The soap bar as claimed in claim 1, comprising 2 to 10%% sodium alumino silicate gel.

4. The soap bar as claimed in claim 1, comprising 25 to 40 wt % water.

5. The soap bar as claimed in claim 1, additionally comprising 0.1 to 6 wt % of an electrolyte.

6. The soap bar as claimed in claim 5, wherein the electrolyte is not a surfactant and is selected from sodium chloride, sodium sulphate, sodium citrate or a mixture thereof.

7. A process to prepare the soap bar as claimed in claim 1, comprising the steps of:
   (a) providing soap,
   (b) providing sodium aluminate,
   (c) providing sodium silicate,
   (d) mixing the soap and a mixture of sodium aluminate and sodium silicate; and
   (e) extruding the mixture to prepare the desired soap bar.

8. The process to prepare the soap bar as claimed in claim 7 wherein the process comprises the steps of:
   (a) including sodium alumino silicate gel in a sigma mixer;
   (b) including soap into the sigma mixer to crush and blend the sodium alumino silicate gel with the soap to prepare a noddle; and
   (c) extruding the noddle through a plodder to prepare the desired soap bar.

9. The process to prepare the soap bar as claimed in claim 8, wherein the sodium alumino silicate gel is prepared outside the sigma mixer by reacting the desired amount of sodium aluminate with sodium silicate.

10. The process to prepare the soap bar as claimed in claim 8, wherein the sodium alumino silicate is prepared in situ in the sigma mixer by reacting the desired amount of sodium aluminate with sodium silicate.

11. The process to prepare the soap bar as claimed in claim 7, wherein the process comprises the steps of:

(a) preparing soap in a plough share mixer or crutcher by reacting desired amount of fatty acid/oil with alkali at 90 to 110° C.;

(b) including sodium alumino silicate gel in the plough share mixer or crutcher to mix with the soap so formed in step (a) with said gel to prepare a mixture;

(c) spray drying the mixture or passing it through a triple roll mill; and (d) then passing it though a plodder to prepare the desired soap bar.

12. The process to prepare the soap bar as claimed in claim 7, wherein the process comprises the steps of:

(a) preparing the sodium alumino silicate is in situ in a plough share mixer or crutcher by reacting the desired amount of sodium aluminate with sodium silicate; followed by (b) preparing soap in the same plough share mixer or crutcher by reacting desired amount of fatty acid/oil with alkali at 90 to 110° C. with constant agitation to prepare a mixture;

(c) spray drying the mixture or passing it through a triple roll mill; and (d) then passing it though a plodder to prepare the desired soap bar.

13. The soap bar as claimed in claim 1, comprising 22 to 40 wt % water.

14. The soap bar as claimed in claims 2, 50 to 70 wt % soap.

15. The soap bar as claimed in claim 3, comprising 2 to 7 wt % sodium alumino silicate gel.

* * * * *